(12) United States Patent
Zustiak et al.

(10) Patent No.: US 10,799,618 B2
(45) Date of Patent: Oct. 13, 2020

(54) METHODS OF TRANSFERRING CARBON NANOTUBES ON A HYDROGEL

(71) Applicant: Saint Louis University, St. Louis, MO (US)

(72) Inventors: Silviya Petrova Zustiak, St. Louis, MO (US); Mozhdeh Imani Nezhad, Richmond Heights, MO (US); Irma Kuljanishvili, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 172 days.

(21) Appl. No.: 15/412,915

(22) Filed: Jan. 23, 2017

(65) Prior Publication Data

US 2017/0210875 A1 Jul. 27, 2017

Related U.S. Application Data

(60) Provisional application No. 62/281,468, filed on Jan. 21, 2016.

(51) Int. Cl.
*A61L 27/52* (2006.01)
*C01B 32/162* (2017.01)
(Continued)

(52) U.S. Cl.
CPC ............ *A61L 27/52* (2013.01); *A61L 27/443* (2013.01); *C01B 32/162* (2017.08); *C01B 32/168* (2017.08); *C08F 122/1006* (2020.02); *C08J 3/212* (2013.01); *C09D 1/00* (2013.01); *C09D 7/61* (2018.01); *C09D 7/67* (2018.01); *A61L 2400/12* (2013.01); *B82Y 5/00* (2013.01); *B82Y 40/00* (2013.01); *C01B 2202/02* (2013.01); *C01B 2202/08* (2013.01); *C01B 2202/22* (2013.01); *C01B 2202/34* (2013.01); *C01B 2202/36* (2013.01); *C08J 2371/02* (2013.01); *C08K 2201/003* (2013.01); *C08K 2201/004* (2013.01); *Y10S 977/742* (2013.01);
(Continued)

(58) Field of Classification Search
CPC ................................ A61K 9/14; A61L 27/52
USPC ......................................................... 424/489
See application file for complete search history.

(56) References Cited

U.S. PATENT DOCUMENTS 7,611,628 B1  11/2009  Hinds, III
7,829,622 B2  11/2010  McDaniel et al.
(Continued)

FOREIGN PATENT DOCUMENTS

KR  2014083266  *  7/2014  .............  B29C 59/02

OTHER PUBLICATIONS

Doring et al., Efficient Transfer of Carbon Nanotubes Using an LOR Resist Sacrificial Layer, Jun. 2013, Micro and Nanosystems, pp. 202-205 (Year: 2013).*
(Continued)

*Primary Examiner* — Dah-Wei D. Yuan
*Assistant Examiner* — Andrew J Bowman
(74) *Attorney, Agent, or Firm* — Stinson LLP

(57) ABSTRACT

Disclosed herein are methods for transferring carbon nanotubes on a hydrogel scaffold. Carbon nanotubes are formed on a substrate and directly transferred onto a hydrogel surface. Carbon nanotubes transferred according to the present disclosure can be used in tissue engineering applications and electrode coating applications.

12 Claims, 9 Drawing Sheets
(4 of 9 Drawing Sheet(s) Filed in Color)

(51) Int. Cl.

| | | |
|---|---|---|
| *C01B 32/168* | (2017.01) | |
| *C08J 3/21* | (2006.01) | |
| *C09D 7/40* | (2018.01) | |
| *C09D 7/61* | (2018.01) | |
| *C09D 1/00* | (2006.01) | |
| *A61L 27/44* | (2006.01) | |
| *C08F 122/10* | (2006.01) | |
| *B82Y 40/00* | (2011.01) | |
| *B82Y 5/00* | (2011.01) | |

(52) U.S. Cl.
CPC ........ *Y10S 977/753* (2013.01); *Y10S 977/842* (2013.01); *Y10S 977/923* (2013.01)

(56) References Cited

U.S. PATENT DOCUMENTS

| | | | | |
|---|---|---|---|---|
| 8,133,465 | B2 * | 3/2012 | Dai ........................ | B82Y 30/00 252/502 |
| 2005/0238810 | A1 * | 10/2005 | Scaringe ................ | B82Y 30/00 427/249.1 |
| 2006/0025515 | A1 | 2/2006 | Scaringe et al. | |
| 2007/0248758 | A1 * | 10/2007 | Ward ..................... | B05D 1/002 427/271 |
| 2012/0076860 | A1 * | 3/2012 | Trout ..................... | A61K 9/14 424/489 |

OTHER PUBLICATIONS

Salavagione et al. (Chemical Sensors basd on polymer composites with carbon nanotubes and graphene:the tole of the polymer, Journal of Materials Chemistry A, No. 2, pp. 14289-14328) (Year: 2014).*

Doring, et al., Efficient Transfer of Carbon Nanotubes Using an Lor Resist Sacrificial Layer, Micro and Nanosystems, ETH Zurich, Switzerland, Transducers 2013, Barcelona, Spain, pp. 16-20.

Bower, et al., Deformation of carbon nanotubes in nanotube-polymer composites, Applied Science letters, vol. 74, No. 22, pp. 3317-3319, May 1999.

* cited by examiner

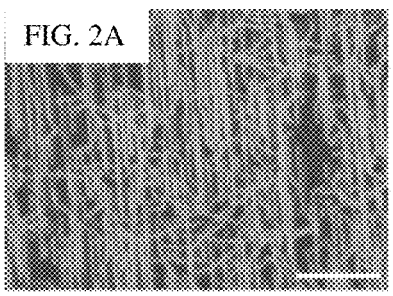
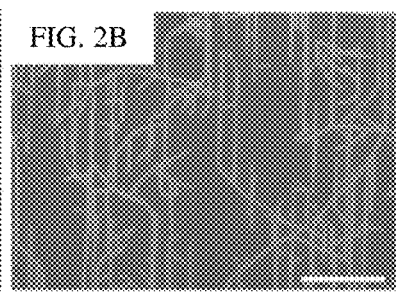
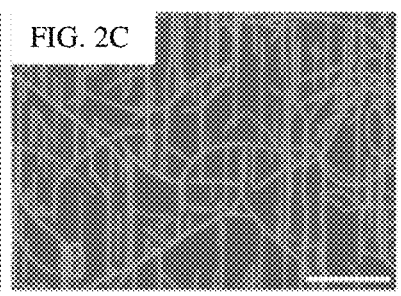

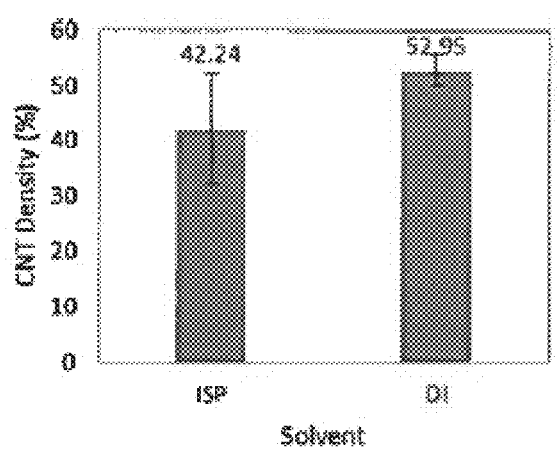
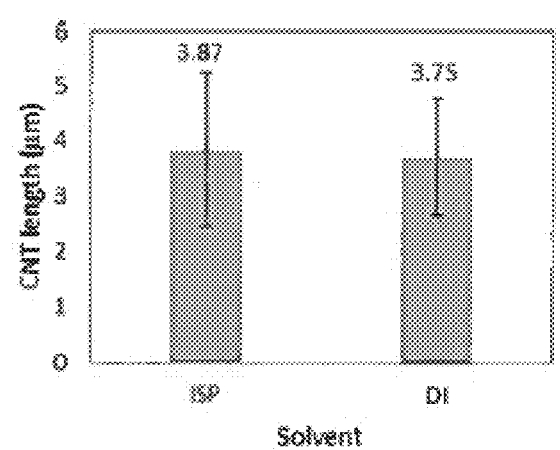
FIG. 3A                    FIG. 3B

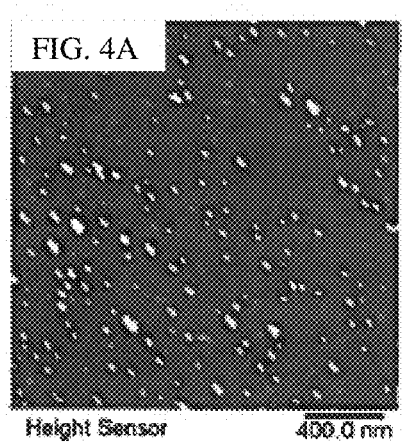 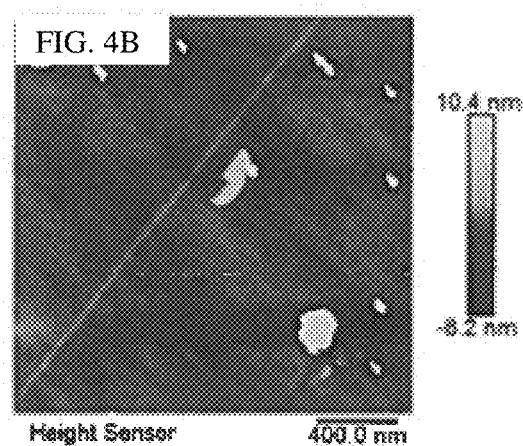

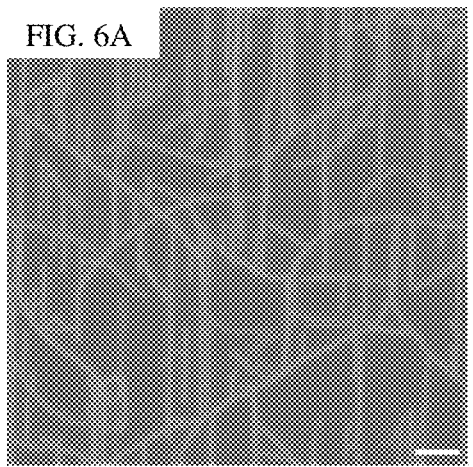 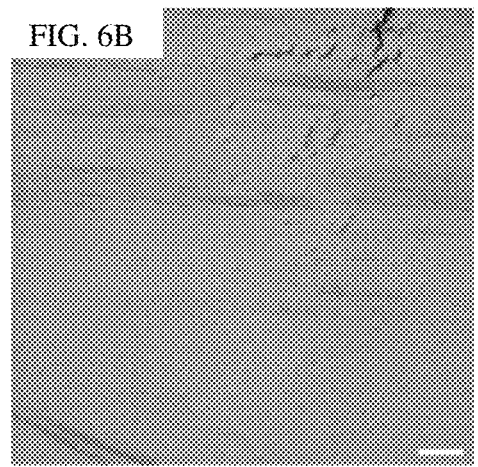 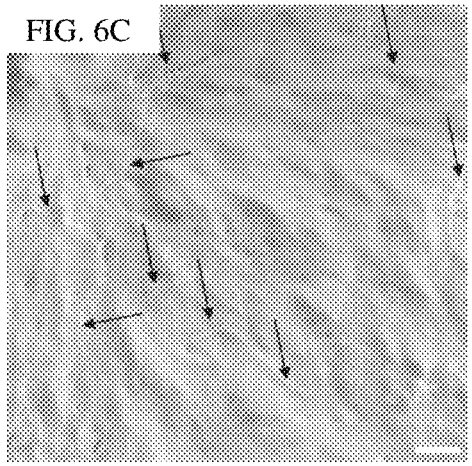 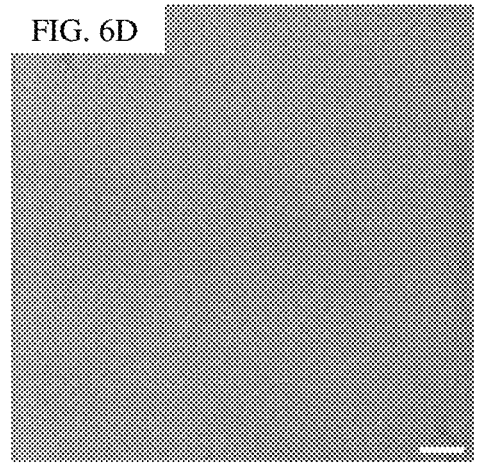

METHODS OF TRANSFERRING CARBON NANOTUBES ON A HYDROGEL

CROSS REFERENCE TO RELATED APPLICATIONS

This application claims priority to U.S. Provisional Patent Application Ser. No. 62/281,468, filed on Jan. 21, 2016, the disclosure of which is hereby incorporated by reference in its entirety.

BACKGROUND OF THE DISCLOSURE

The present disclosure generally relates to tissue engineering. More particularly, the present disclosure is directed to methods for transferring carbon nanotubes. Carbon nanotubes transferred according to the present disclosure can be used in tissue engineering applications. Patterned and aligned carbon nanotubes can promote directional cell growth. Hydrogels are ideal substrates for soft tissue engineering applications such as neural tissue engineering since they closely emulate soft tissues. Carbon nanotubes transferred according to the present disclosure can also be used in electrode coating applications.

Carbon nanotubes (CNTs) have an outstanding potential for medical and electrical applications due to their unique structure—hollow cylinders made of graphene sheets, their excellent electrical conductivity, high aspect ratio, and unique mechanical properties—strong, yet flexible. CNTs are produced as single walled carbon nanotubes (SWCNTs) or multi-walled carbon nanotubes (MWCNTs) consisting of one or multiple concentrically rolled layers of graphene, respectively. The diameter of SWCNTs is close to 1 nm while the diameter of MWCNTs could be as high as 50 nm.

Both SWCNTs and MWCNTs have been explored for use in biomedical applications, such as tissue engineering and drug delivery. While non-toxic, there are some concerns with CNTs biocompatibility mostly because of their stability (they are non-degradable) and high aspect ratio which has been found to cause tumor formation when CNTs are administered at a high dose. However, at small doses or when attached to a surface or embedded into a biomaterial, CNTs have been found biocompatible.

CNTs have been extensively studied for their beneficial use in neural tissue engineering, including CNT-based scaffolds to drive nerve regeneration across a lesion site. Hydrogels are ideal candidates for many biological applications due to their highly hydrophilic nature and properties closely mimicking native soft tissues.

However, aligning CNTs in a biologically-relevant scaffold to enhance the topography guidance effect on the cellular outgrowth for tissue engineering applications such as for neurite outgrowth still remains a challenge. Aligning CNTs on hydrogel scaffolds is particularly difficult and it typically involves a multistep process. Accordingly, there exists a need to develop methods for aligning CNTs in biologically-compatible scaffolds for tissue engineering applications and electrical applications.

BRIEF DESCRIPTION OF THE DISCLOSURE

The present disclosure is generally related to transferring carbon nanotubes without the use of a sacrificial layer. More particularly, the present disclosure is directed to methods for transferring carbon nanotubes in a single step. The method can be used for various applications such as, for example, neural regeneration, electrode coating and cardiomyocyte cell growth.

In one aspect, the present disclosure is directed to a method for transferring carbon nanotubes. The method includes: providing a substrate; preparing a carbon nanotube on the substrate to prepare a carbon nanotube-coated substrate; applying a hydrogel precursor solution to the carbon nanotube-coated substrate; polymerizing the hydrogel precursor solution to form a hydrogel; and removing the hydrogel from the substrate, wherein the hydrogel comprises the carbon nanotubes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIGS. 2A-2C depict SEM images of CNTs grown with DI water solvent for 14 minutes (FIG. 2A), CNTS grown with ISP solvent for 7 minutes (FIG. 2B) and CNTS grown with ISP solvent for 14 minutes (FIG. 2C). Scale bar is 2 µm.

FIGS. 3A & 3B are graphs depicting the density of SWCNTs grown in DI water and ISP (FIG. 3A) and the length of SWCNTs grown in DI water and ISP (FIG. 3B).

FIGS. 4A & 4B depict atomic force microscopy (AFM) images of SWCNTs grown in DI water (FIG. 4A) and ISP (FIG. 4B) showing more residuals remaining on the quartz wafer in the DI water condition as compared to the ISP condition.

FIGS. 6A-6D depict SEM images of SWCNTs grown on quartz substrate (FIG. 6A); PEG hydrogel soaked in deionized water for 72 hours (FIG. 6B); SWCNTs transferred onto a PEG hydrogel (FIG. 6C); and quartz substrate after SWCNT transfer (FIG. 6D).

DETAILED DESCRIPTION

Figure 1:
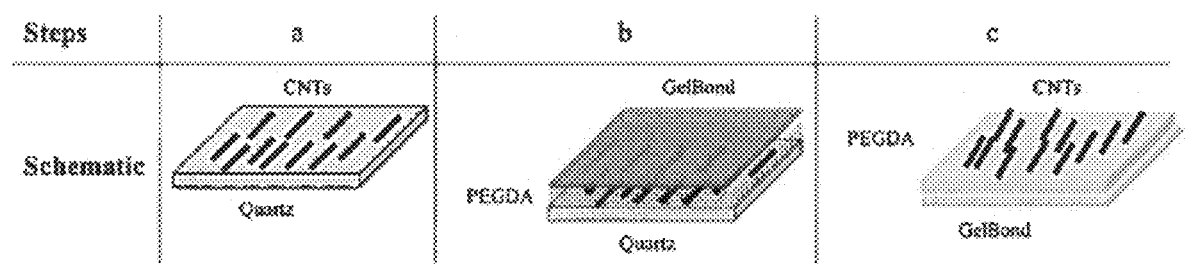
FIG. 1 illustrates the method for transferring quartz-grown SWCNTs onto a polyethylene glycol diacrylate (PEGDA) hydrogel. Aligned SWCNTs were grown on a quartz wafer (Step a). In order to transfer the CNTs from the quartz wafer onto the PEGDA hydrogel, 25 µL of the PEGDA gel precursor solution was deposited directly on the wafer and sandwiched with a gel support material (e.g., GELBOND®) of matching dimensions, hydrophilic side-down (Step b). The samples were soaked in DI water and then the gel support film/PEGDA was peeled off from the quartz substrate (Step c).

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Disclosed are methods for transferring carbon nanotubes. Carbon nanotubes transferred according to the present disclosure can be used in tissue engineering applications and electrical applications. For example, CNTs have excellent electrical conductivity, which is beneficial for excitable tissues such as neural tissues, strong mechanical properties and morphological similarity to neurites. Patterned and aligned CNTs can promote directional cell growth, which is particularly suitable for promoting neural growth. Hydrogels are ideal substrates for CNT alignment since they closely emulate soft tissues such as brain. Also disclosed are methods for the alignment of CNTs onto a hydrogel (e.g., PEG) scaffold. In the first step, CNTs are aligned onto a substrate (e.g., quartz wafer) and in the second step the aligned CNTs are directly transferred onto a PEG hydrogel surface.

In one aspect, the present disclosure is directed to a method for transferring carbon nanotubes. The method includes: providing a substrate; preparing a carbon nanotube on the substrate to prepare a carbon nanotube-coated substrate; applying a hydrogel precursor solution to the carbon nanotube-coated substrate; polymerizing the hydrogel precursor solution to form a hydrogel; and removing the hydrogel from the substrate, wherein the hydrogel comprises the carbon nanotube.

In one embodiment, the method can be used to transfer single wall carbon nanotubes. Suitable single wall carbon nanotubes have diameters ranging from about 1 nm to about 3 nm. In another embodiment, the method can be used to transfer multiwall carbon nanotubes.

The density of the carbon nanotubes can range from about 25% to about 55%.

The lengths of the carbon nanotubes can range from about 2 μm to about 5 μm.

Carbon nanotubes can be prepared on the substrate using methods known to those skilled in the art. A particularly suitable method includes coating the substrate with an iron catalyst solution. Other suitable metals for metal catalyst solutions can be, for example, nickel, chromium, copper, platinum, palladium, gold, silica and clusters or large particles made from metal alloys from cobalt and tungsten. The substrate can be coated by dipping the substrate in an iron catalyst solution. The iron catalyst solution can also be applied to a surface of the substrate. A particularly suitable method for applying the iron catalyst solution to the surface of the substrate is by spin coating. After the substrate is coated with the iron catalyst solution, the substrate is transferred to a chemical vapor deposition (CVD) furnace. Samples are purged with about 1000 sccm argon at room temperature, ramped up to about 875° C. in the presence of about 400 sccm argon and about 200 sccm hydrogen. The catalyst is then reduced in the presence of hydrogen at about 600 sccm. Carbon nanotubes are grown by flowing methane at about 900 sccm and hydrogen at about 100 sccm for a desired period of time. Particularly suitable times can range from about 7 minutes to about 14 minutes. The system is then cooled to room temperature in the presence of argon and hydrogen.

The iron catalyst solution can be prepared using a solvent selected from water, alcohols, polyvinylpyrrolidone (PVP), ethanol, dimethylformamide (DMF), and glycerol. Particularly suitable water is deionized (DI) water. Suitable alcohols include ethanol, methanol and isopropyl. A particularly suitable alcohol is isopropyl (ISP). Catalyst solution contains iron salt such as $(Fe(NO_3)_3 \cdot 9H_2O$ (iron nitrate nonahydrate) dissolved in a solvent, such as water and isopropyl alcohol. Iron nitrate nonhydrate can be used to prepare master solutions with solute concentration of about 0.5 mM DI water in one exemplary master solution embodiment and about 0.75 mM isopropyl in another master solution exemplary embodiment. The master solutions are further diluted with DI water and ISP at a volume ratio of about 1:1.

In one embodiment, the method further includes aligning the carbon nanotube on the substrate. CNT growth and alignment on a quartz wafer substrate is preferably performed at a temperature greater than 573° C., and more preferably at a temperature of about 900° C. CNT growth and alignment can be analyzed by scanning electron microscopy (SEM) and analysis of SEM images. SEM images can be analyzed using ImageJ software, for example.

Suitable substrates include, for example, quartz wafers, silicon wafers, $Si/SiO_2$ wafers, fused quartz, sapphire wafers, and other substrates for carbon nanotube growth. A particularly suitable substrate can be a quartz substrate. The quartz substrate can be a quartz wafer. Prior to carbon nanotube growth, the quartz substrate can be annealed in the CVD furnace with the flow of hydrogen gas to achieve a reduction of the catalyst to Fe particles.

The hydrogel precursor solution can be prepared and polymerization can be performed using methods known to one skilled in the art. To generate PEG hydrogels, individual PEG chains that have been functionalized with two or more crosslinkable groups, such as acrylates, are dissolved in aqueous solution, mixed with appropriate photoinitiator and exposed to UV or visible light. The acrylate groups cross-link via free radical polymerization to form an insoluble hydrogel network. A particularly suitable exemplary embodiment includes preparing a 1% w/v stock solution of initiator dissolved in DI water and a 30% w/v polyethylene glycol stock solution in phosphate buffered saline. Photoinitiator (0.1% w/v final concentration) and 1×PBS is added to the polyethylene glycol solution and mixed to achieve a final concentration of 10% w/v polyethylene glycol.

Particularly suitable hydrogels include natural and synthetic hydrogels including combinations of natural and synthetic hydrogels. Suitable natural hydrogels include, for example, alginate, chitosan, silk, agarose, collagen, gelatin, fibrinogen, fibrin, laminin, fibronectin, carboxymethyl cellulose, hyaluronan, and combinations thereof. Suitable synthetic hydrogels include, for example, polyvinyl alcohol (PVA), pHEMA, poly-lactic-co-glycolic acid, polylactic acid, polyglycolic acid, polyacrylamide, polypropylene glycol, polyurethane, polyvinylpyrrolidone, methyl cellulose, and co-polymers thereof. Suitable hydrogels also include, for example, poly(ethylene glycol)-based (PEG-based) hydrogels. PEG is FDA approved for a variety of applications and exhibits high biocompatibility and little or no immunogenicity. Particularly suitable PEG-based hydrogels include, for example, poly(ethylene glycol) diacrylate (PEGDA), PEG-vinyl sulfone, PEG-amine, PEG-dimethacrylate, PEG-dithiol, PEG-polylactic acid co-polymers (PEG-PLA), PEG-maleimide, PEG-biotin, PEG-butyraldehyde, PEG-carboxymethyl, where all PEGs could be single chain or multiarm, as well as can possess homofunctionality or heterofunctionality Suitable photoinitiators are known to one skilled in the art and can be, for example, 2,2 dimethoxy-2-phenyl acetophenone, acetophenone, anisoin, anthraquinone, benzene tricarbonylchromium, benzyl, benzoin, benzoin ethyl ether, benzoin methyl ether, benzophenone, 4-benzoylbiphenyl, camphorquinone, 2-chlorothioxanthen-9-one, dibenzosuberenone, ferrocene, hydroxyacetophenone, methylbenzophenone, phenanthrenequinone, thioxanthen-9-one, and combinations thereof. A particularly suitable photoinitiator can be IRGACURE® (commercially available from BASF, Florham Park, N.J.).

The method can further include applying a gel support material to the hydrogel precursor solution. Suitable gel support materials include, for example glass support materials such as, for example, glass coverslips. Other suitable gel support materials include polymeric films such as, for example, polyester films. A particularly suitable polymeric film is GELBOND® (commercially available from Lonza, Basel, Switzerland). When using GELBOND®, the hydrophilic side is placed in contact with the hydrogel precursor solution, which then adheres to the hydrogel upon polymerization (gelation).

The method further includes polymerizing the hydrogel precursor solution to form a hydrogel. The polymerization processes can take between about 1 and about 20 minutes of illumination, depending on the photoinitiator and the intensity of the light source, and can be conducted under mild conditions. Polymerization can occur by exposing the solution to ultraviolet (365 nm) light (4.81 $\mu W/cm^2$) for 10 minutes. As known to those skilled in the art, polymerization can also occur without the use of a photoinitiator. For example, polymerization can occur by merely incubating the hydrogel precursor solution for a period of time until polymerization and hydrogel formation occurs. Polymerization can also be achieved using chemical initiators. Polymerization can also be achieved by applying heat to the hydrogel precursor solution.

The method further includes removing the hydrogel from the substrate, wherein the hydrogel comprises the carbon nanotube. Following polymerization to form the hydrogel, the hydrogel/gel support material (e.g., GELBOND®) can be soaked in water prior to peeling the hydrogel/gel support material from the substrate (e.g., quartz wafer). The carbon nanotubes are contained in the hydrogel.

The method can further include contacting a cell with the hydrogel comprising the carbon nanotube and culturing the cell.

Any cell can be contacted with the hydrogel. Particularly suitable cells include adherent cell types such as, for example, neuronal cells, muscle cells, fibroblast cells, bone cells, epithelial cells, lung cells, breast cells, hepatic cells, cardiac cells, and combinations thereof.

The method for preparing carbon nanotubes on a substrate includes: providing a substrate; annealing the substrate at a temperature greater than 573° C.; cooling the substrate; contacting the substrate with an iron nitrate solution, wherein the iron nitrate solution comprises isopropyl alcohol; transferring the substrate contacted with the iron nitrate solution into a chemical vapor deposition furnace; and growing carbon nanotubes by flowing methane and hydrogen over the substrate.

Suitable substrates include, for example, quartz wafers, silicon wafers, Si/SiO2 wafers, fused quartz, sapphire wafers, and other substrates for carbon nanotube growth. A particularly suitable substrate includes quartz wafers.

A particularly suitable iron nitrate solution includes $Fe(NO_3)_3$ $9H_2O$, Iron(III) Nitrate nonahydrate in isopropyl alcohol. For example, a master solution can be made with 0.7 mg of $Fe(NO_3)_3$ of iron salt dissolved in 10 milliliters of any solvent. Master solution can further be dissolved to reduce the concentration as desired for specific applications. The master solution can be prepared with different solvents such as, for example, PVP, Water, Ethanol, DMF, Glycerol, and with a specific range of concentration. In addition to using iron for carbon nanotube formation, other suitable metals such as, for example, nickel, chromium, copper, platinum, palladium, gold, silica and clusters or large particles made from metal alloys from cobalt and tungsten can be used.

Suitable annealing temperatures include greater than 573° C. Particularly suitable annealing temperatures range from greater than 573° C. to about 900° C. A particularly suitable annealing temperature is about 900° C.

Suitable flow of methane includes about 900 sccm. Suitable growth time ranges from about 7 minutes to about 14 minutes.

Suitable flow of hydrogen includes about 100 sccm. Suitable growth time is ranges from about 7 minutes to about 14 minutes.

Suitable methods for contacting the substrate with the iron nitrate solution includes dip-coating the substrate in the iron nitrate solution, pipetting the iron nitrate solution onto a surface of the substrate, spraying the iron nitrate solution on a surface of the substrate, and combinations thereof.

In a particularly suitable embodiment, the method includes providing a quartz wafer substrate; annealing the quartz wafer substrate at a temperature of about 900° C.; cooling the quartz wafer substrate to about room temperature; contacting the quartz wafer substrate with an iron nitrate solution, wherein the iron nitrate solution comprises isopropyl alcohol; transferring the quartz wafer substrate contacted with the iron nitrate solution into a chemical vapor deposition furnace; and growing carbon nanotubes by flowing methane and hydrogen over the substrate.

Suitable flow of methane includes about 900 sccm. Suitable flow of hydrogen includes about 100 sccm. Suitable growth time is from about 7 minutes to about 14 minutes.

EXAMPLES

Materials and Methods

Iron trinitrate nonahydrate ($Fe(NO_3)_3$ $9H_2O$, $M_w$=404.0) was purchased from Sigma Aldrich (St Louis, Mo.). Isopropyl alcohol 99% ($M_w$=60.10) was purchased from Fisher Scientific (Waltham, Mass.). Stable temperature (ST) cut quartz wafers with D=76.2 mm, and thickness of 500 um were purchased from University Wafer (Boston, Mass.).

Poly(ethylene glycol) diacrylate (PEGDA) ($M_w$=5000 Da) was purchased from Laysan Bio (Arab, Ala.). Phosphate buffer solution (PBS) 10×, pH 7.4 was purchased from Thermo Scientific (Waltham, Mass.). IRGACURE® 2959 was purchased from BASF Corporation (Florham Park, N.J.).

Annealing of Quartz and Growth of Aligned Single-Walled Carbon Nanotubes

Prior to CNT growth, the quartz wafer was annealed in a furnace for 12 hours with a thermal ramp of 5° C./mm to 900° C., and was cooled down to room temperature in the presence of air. The Single-Walled Carbon Nanotubes (SW-CNTs) were prepared by dip coating the quartz wafer into Fe catalyst in a chemical vapor deposition (CVD) furnace. Prior to dip coating, the quartz substrates were washed into deionized (DI) water, acetone, and isopropanol with sonication for 3 mm and dried prior to the Fe catalyst coating. To prepare the catalyst, iron salt-based [$Fe(NO_3)_3$] nanoparticles was used. The master solution of Fe catalyst solution was prepared 24 hours prior to dip coating. In this study, the ferric nitrate was used to prepare master solution with solute concentration of 0.5 mM in DI water and 0.75 mM in isopropyl (ISP). In order to dip coat the quartz wafer, the master solutions were further diluted with DI water and isopropyl at a volume ratio of 1:1. The substrates were dipped into Fe-based molecular solutions for 20 seconds. After dip coating, the substrates were loaded into a ceramic boat and transferred to the CVD system. The samples were purged with 1000 sccm argon for 5 mm at room temperature, and ramped up to 875° C. in the presence of 400 sccm argon and 200 sccm hydrogen. Before introducing methane, the catalyst was reduced in the presence of hydrogen at 600 sccm for 10 mm. Carbon nanotubes were grown by flowing of methane at 900 sccm and hydrogen at 100 sccm for 7 minutes and 14 minutes, and the system was cooled down to room temperature in the presence of argon and hydrogen. SWCNTs alignment and density were quantified from scanning electron microscope (SEM) images with ImageJ free software. For SEM imaging, the samples were oven dried at 60° C., sputter coated (SCD 005, Bal-Tec, Leica Microsystems, Buffalo Grove, Ill.) with gold and imaged via SEM (Zeiss EVO LSIS SEM, Oberkochen, Germany) Images were taken at a low voltage of 1-1.5 kV at various magnifications under a high vacuum environment.

Polyethylene Glycol Hydrogel Preparation

First, stock solution of 1% w/v IRGACURE® was prepared by dissolving IRGACURE® in DI water, and sonicating for 1 hour. Next, a 30% w/v stock solution of PEGDA was prepared by dissolution in phosphate buffered saline (1×PBS, pH 7.4). Photoinitiator (IRGACURE®, 0.1% w/v final concentration) and 1×PBS were added to the PEGDA solution and mixed thoroughly to achieve a final concentration of 10% w/v PEGDA. The samples were exposed to 365 nm ultraviolet (UV) light (4.81 $\mu W/cm^2$) for 10 mm to achieve gelation.

Example 1

Method for Transferring CNT

In this Example, the method for transferring CNTs from a quartz wafer onto PEGDA Hydrogel was developed.

Aligned SWCNTs were grown on a quartz wafer (illustrated in FIG. 1, step a). 25 µL of a PEGDA gel precursor solution was deposited directly on the quartz wafer and sandwiched with GELBOND® (hydrophilic side-down) having dimensions matching the quartz wafer (FIG. 1, step b). Upon gelation, the sample was soaked in DI water for 30 minutes and the GELBOND®/PEGDA was peeled off the quartz substrate (FIG. 1, step c).

Example 2

Hydrogel Swelling and Mesh Size

In this Example, the swollen mass and dry mass were determined to obtain the mass swelling ratio.

Hydrogels were soaked in DI water for 24 hours, and after carefully blotting excess water with a KimWipe, the samples were weighted, to give the swollen mass, $M_s$. The samples were then placed in an oven at 60° C. for 48 hours and then weighed, to give the dry mass, $M_d$. The mass swelling ratio, $Q_M$, was determined by:

$$Q_M = \left(\frac{M_s}{M_d}\right) \qquad \text{Equation (1)}$$

The modified Flory-Rehner theory was used to determine the mesh size, $\xi$, for neutral hydrogel prepared in water by first calculating the molecular weight between cross links, $M_c$:

$$\frac{1}{M_c} = \frac{2}{M_n} - \frac{\left(\frac{\overline{V}}{V_1}\right)[\ln(1-v_{2,s})+v_{2,s}+\chi_1 v_{2,s}^2]}{v_{2,r}\left[\left(\frac{v_{2,x}}{v_{2,r}}\right)^{\frac{1}{3}}-\left(\frac{v_{2,x}}{v_{2,r}}\right)\right]} \qquad \text{Equation (2)}$$

where $M_n$ is the molecular weight of the uncrosslinked polymer, $\overline{V}$ is the specific volume of the polymer, $V_1$ is the molar volume of the solvent (18 $cm^3$ $mol^{-1}$ for water), $V_{2,s}$ is the polymer volume fraction in the swollen hydrogel, $V_{2,r}$ is the polymer volume fraction in the hydrogel is immediately upon crosslinking, and $\Phi 1$ is the interaction parameter between the polymer and the solvent (0.426 for PEG in water). The mesh size was then determined by first calculating the root mean square end-to-end distance of the polymer chain:

$$\sqrt{r_0^2} = lC_n^{1/2}n^{1/2} \qquad \text{Equation (3)}$$

where l is the average bond length (0.146 nm), $C_n$ is the characteristic ratio of the PEG polymer (4.0), and n is the number of bonds present in the crosslink calculated by:

$$n = 2\frac{M_c}{M_r} \qquad \text{Equation (4)}$$

where $M_r$ is the repeat unit molecular weight for the PEG polymer (44 g $mol^{-1}$ for PEG). Finally, the mesh size was determined by the following equation:

$$\xi = v_2^{-1/3}(r_0^2)^{1/2} \qquad \text{Equation (5)}$$

Statistical Analysis

Results are reported as averages±standard deviation. Statistical significance between multiple samples was tested by ANOVA and between two samples by a student's t-test ($p<0.05$) followed by a post-hoc analysis. A minimum of three samples from three independent experiments were tested per condition.

Results and Discussion

Growth of Carbon Nanotubes as a Function of Time, and Solvent

SWCNTs were produced from iron nitrate solution on a quartz wafer by CVD at 900° C. Aligned CNT growth on a quartz wafer at temperatures higher than 573° C. resulted in phase transition of the single crystal quartz wafer from alpha to beta quartz. Also, high annealing temperatures, such as 900° C., of quartz improved CNT alignment. Iron salts were used to produce high-quality, high density, aligned SWCNTs. Two growth times were developed to adjust SWCNTs density. In all cases high densities of catalytic nanoparticles achieved higher density of grown CNTs. FIGS. 2A-2C show SEM images of aligned SWCNTs grown on a quartz wafer in DI water (for 7 minutes) and ISP solvent (for 7 minutes and 14 minutes), respectively.

The DI water and ISP were chosen because they are efficient solvents in which catalyst particles are miscible. No precipitation of the catalyst was observed in the DI water and ISP solvents after 24 hours. While both solvents were efficient, a slight difference was observed in the resultant SWCNTs growth. The samples prepared with DI water had slightly higher density (52.95%), and lower length (3.75 μm) of SWCNTs as compared to the samples with ISP (FIGS. 3A & 3B). However, the differences were not statistically significant—both solvents led to the growth of dense SWCNTs of high aspect ratio (note that length is in micrometers, while radius is in nanometers).

Next, the SWCNTs were examined under an atomic force microscope (AFM, Bruker) (FIG. 4A & 4B). Two phenomena were noted from the AFM images. First, the DI water sample had overall more residuals but the residuals were smaller in size, while the ISP solvent sample had less residuals but the residuals were larger in size. The lower amount of residuals in the ISP solvent was attributed to a more uniform evaporation rate at room temperature compared to DI water. Without being bound by theory, the lower amount of residuals in the ISP solvent could be partially responsible for the slightly higher SWCNT length in the ISP solvent. Another reason could be the ability of ISP to keep Fe nanoparticles active for nucleation and hence enable SWCNT growth. Another observation from the AFM images was that the SWCNTs appeared to grow perpendicular to the quartz striations and not along them.

Example 3

In this Example, SWCNT growth as a function of growth time was analyzed.

Figure 5A:
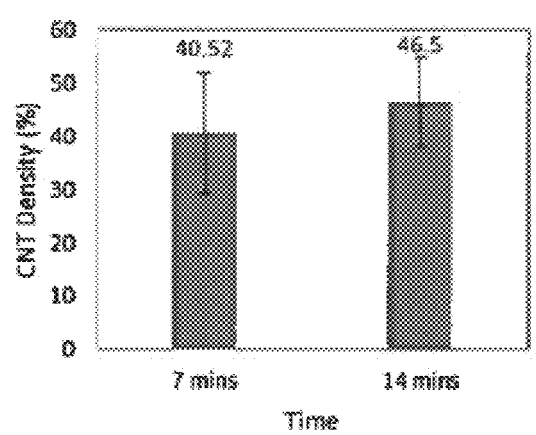
FIGS. 5A & 5B are graphs depicting the density of SWCNTs as a function of time (7 minutes vs 14 minutes) grown in ISP, showing higher density of SWCNTs grown for 14 minutes as compared to 7 minutes (FIG. 5A), and length of SWCNTs as a function of time (7 minutes vs 14 minutes) grown in ISP (FIG. 5B) showing longer length of SWCNTs grown for 14 minutes as compared to 7 minutes.
Figure 5B:
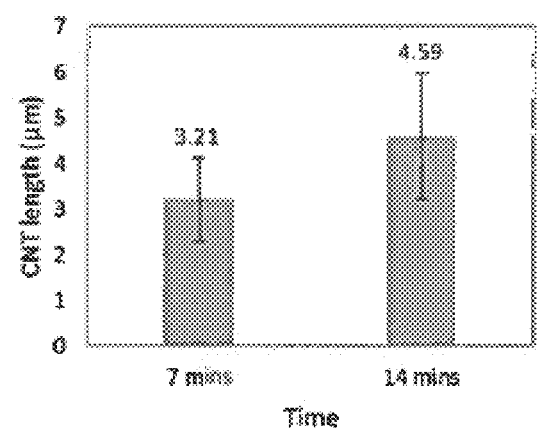

It was expected that longer growth times would lead to higher density, but also raised the concern that growth time would affect the length and alignment of the SWCNTs. For example, it has been shown that longer growth times can affect alignment, because, after introducing the carbon precursor, the catalysts could move widely to form aligned SWCNT. The results indicate that enhancement in the quantity of SWCNTs were observed with an increase in growth time (FIGS. 5A & 5B). By doubling the growth time, the density of SWCNT was increased by about 13%, and the SWCNTs length was increased by about 30%. Furthermore, alignment was not compromised (data not shown) and hence 14 minute growth time was used for further experiments.

Example 4

In this Example, the transfer of SWCNTs grown on quartz wafer onto a hydrogel by a single step method was investigated (refer to FIG. 1).

FIGS. 6A-6D depict SEM images of SWCNTs on a quartz wafer, plain PEG hydrogel, a quartz after the SWCNTs were transferred, and the SWCNTs transferred onto a PEG hydrogel. The images indicate that the quartz wafer had no residual SWCNTs upon transfer (compare FIGS. 6A and 6C). The results indicated that the transfer of SWCNTs under the conditions was highly efficient as indicated by the lack of SWCNTs remaining on the quartz wafer upon transfer. The results also indicated that the SWCNTs were partially embedded in the hydrogel after the transfer. This may be because the transfer method involved depositing a hydrogel precursor solution on top of the SWCNTs, which was subsequently gelled entrapping the SWCNTs inside. Note that the PEG hydrogel used had a swelling ratio of about 15 and a mesh size of about 10 nm, while the SWCNTs had a diameter of about 1.8 nm and a length of about 4.6 μm. Thus, it was possible for the hydrogel to entrap the high aspect ratio SWCNTs inside the hydrogel bulk, yet, near the surface upon gelation. The residuals noted on the plain hydrogel prior to SWCNTs transfer were attributed to the buffer salts (1×PBS) and the IRGACURE® photoinitiator. Their number was greatly reduced upon transfer because the transfer step included soaking the hydrogels in DI water which should result in dilution of both salts and IRGACURE®.

Example 5

In this Example, cell adhesion was used as an indirect measure of successful SWCNT transfer from a substrate.

Two different cell lines were used, neural-like PC12 cells and human lung cancer A549 cells, to determine whether cell type affected cell adhesion on SWCNTs. Cell adhesion was used as an indirect measure of successful SWCNT transfer for two reasons: (1) the hydrogels used in this Example were synthetic and completely inert, thus, presenting no adhesion sites for cell attachment, and (2) cells will attach to unmodified CNTs. Therefore, cells could only adhere to the hydrogel substrate if the SWCNT transfer from the quartz onto the hydrogel was successful.

Figures 7A, 7B, 7C, 7D, 7E, 7F, 7G, 7H, 7I, 7J:
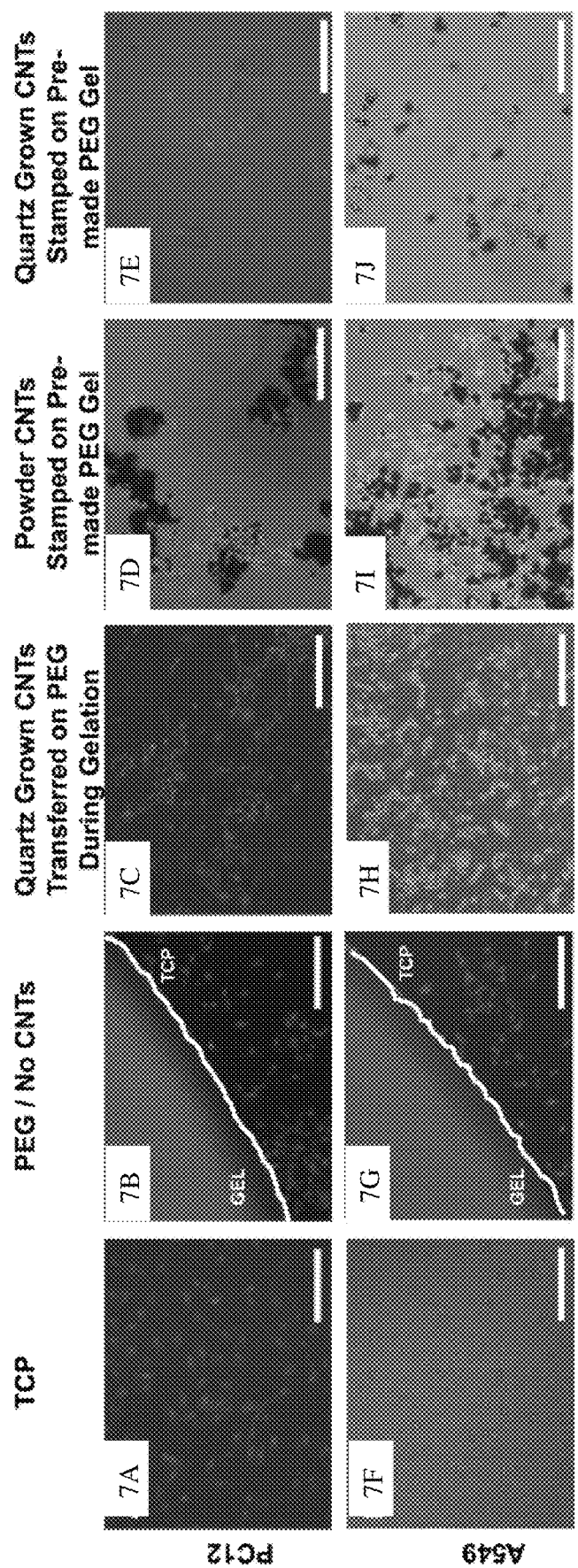
FIGS. 7A-7J are phase contrast images of PC12 (upper row) and A549 (bottom row) cells on various substrates: tissue culture polystyrene (TCP) (FIGS. 7A & 7F); plain PEG 2 hydrogel, where the hydrogel edge is marked by a white line (FIGS. 7B & 7G); PEG 2 hydrogel with transferred SWCNTs (FIGS. 7C & 7H); PEG 2 hydrogels where powder MWCNTs were mechanically stamped on the pre-swollen hydrogels (FIGS. 7D & 7I); PEG 2 hydrogels where the quartz-grown SWCNTs were stamped onto the pre-swollen gels (FIGS. 7E & 7J). Scale bars=100

To investigate the successful SWCNT transfer onto a hydrogel through cell adhesion, we used PEG 2 hydrogel as an example (FIG. 7). PEG hydrogel was chosen because it is biocompatible, tunable, has mechanical properties similar to those of many soft biological tissues and, importantly, PEG is inert and PEG alone does not support cell adhesion. Neither PC12, nor A549 cells were able to attach to the plain PEG hydrogels (FIGS. 7B & 7G). However, cells were able to grow on the TCP in the immediate vicinity of the hydrogels, indicating that the lack of cells on the hydrogels' surface was not due to gel cytotoxicity, but rather lack of cell attachment sites. On the other hand, when cells were grown on the surface of hydrogels with transferred SWCNTs, excellent cell attachment and spreading (FIGS. 7C & 7H) were noted comparable to that of cells grown on TCP (FIGS. 7A & 7F).

Because SWCNTs had a diameter of <2 nm, it was not possible to visualize them via optical microcopy to confirm that the cells were colocalized with the SWCNTs. Thus, to further confirm that cells were attached to the hydrogels because of the transferred SWCNTs, the cells were also seeded on the surface of PEG gels where aggregates of powder MWCNTs were physically embedded in the gel by pressing preformed gels onto the MWCNT powder (FIGS. 7D & 7I). The results indicated that cells attached to the MWCNT-rich hydrogel regions (black regions in images) and not to the hydrogel regions devoid of MWCNTs.

To demonstrate that the in situ gelation step was important for efficient SWCNTs transfer, cell attachment on hydrogels formed onto the quartz substrate were compared to preformed hydrogels that were subsequently "stamped" onto the quartz substrate bearing the SWCNTs. A much lower cell density was found on the preformed hydrogels (FIGS. 7E & 7J) compared to the in situ formed hydrogels (FIGS. 7C & 7H), indicating that the SWCNT transfer efficiency was substantially lower in the former case. Hence, an interaction between the soluble polymer molecules in the polymer precursor solution and the SWCNTs and/or the physically entrapped SWCNTs during gelation was responsible for the incorporation of the SWCNTs onto the hydrogel surface.

Example 6

In this Example, properties, chemical structures, and reaction mechanisms of PEGDA, PA, and PVA were determined.

Figure 8A:
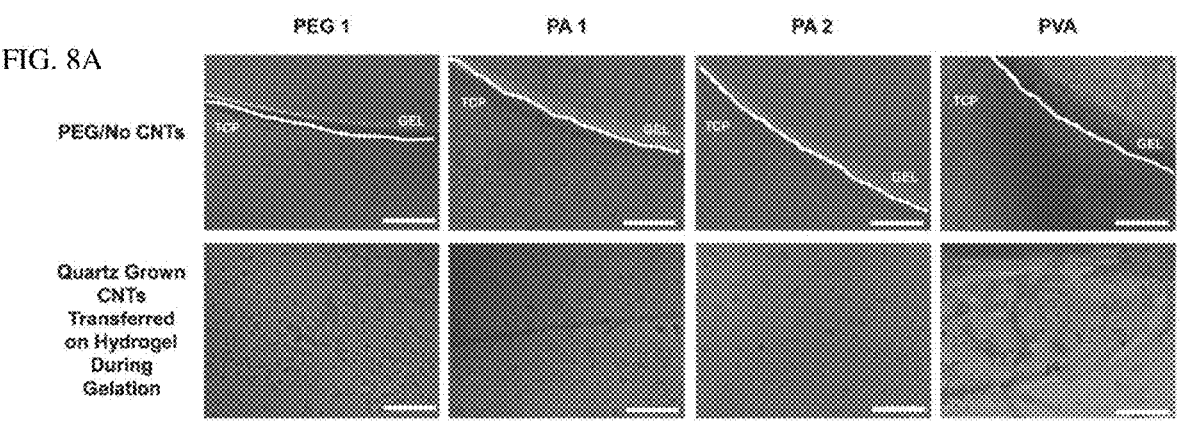
FIG. 8A are phase contrast images of A549 cells adhered on different various hydrogels without SWCNTs (upper row) or with transferred SWCNTs (bottom row). Scale bars=100 μm.
Figure 8B:
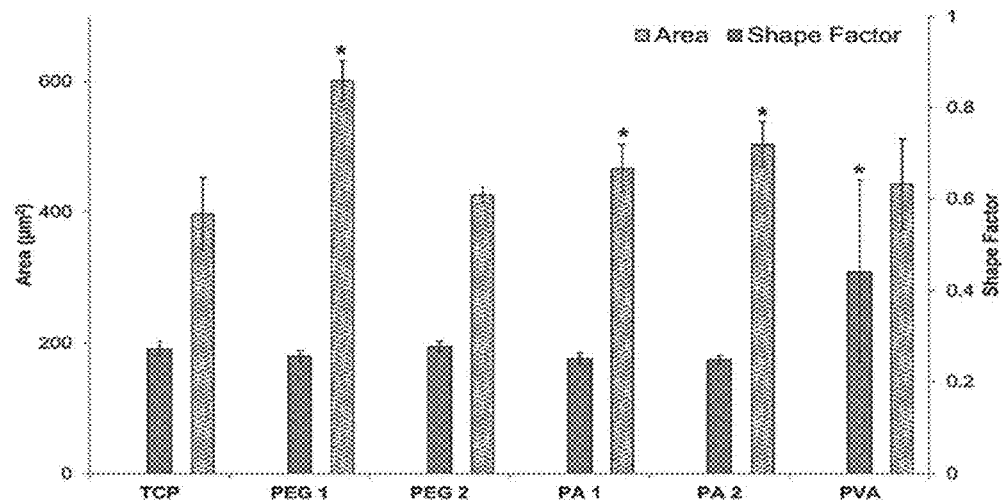
FIG. 8B are graphs depicting spreading area and shape factor of A549 cells on TCP and various hydrogels with transferred SWCNTs. Images were analyzed with ImageJ. Significant differences from cells on TCP are designated by an asterisk, where 120 cells were analyzed per condition (n=3, p<0.05).

To vary hydrogel physical (e.g., swelling) and mechanical (e.g., modulus) properties, varying polymer concentrations were tested. Note that A549 cells were able to spread on all SWCNT-hydrogel composites (FIG. 8A, bottom row) and not on the hydrogels alone (FIG. 8A, top row). However, the highest spreading area was observed on the PEG 1 hydrogel, closely followed by the spreading area on the two PA gels (statistically higher than TCP, $p<0.05$) (FIG. 8B). Also, the cells on the PVA hydrogels appeared more rounded (higher shape factor) than cells on TCP or the other SWCNT-hydrogel nanocomposites, indicating potentially lower density of cell attachment sites (i.e., lower density of transferred SWCNTs) compared to the rest of the hydrogels tested. These results indicated that successful SWCNT transfer was possible on hydrogels of various polymer concentrations as well as physical and mechanical properties.

Example 7

In this Example, cell viability on PEG 2 SWCNTs nancomposites was determined.

Figures 9A, 9B:
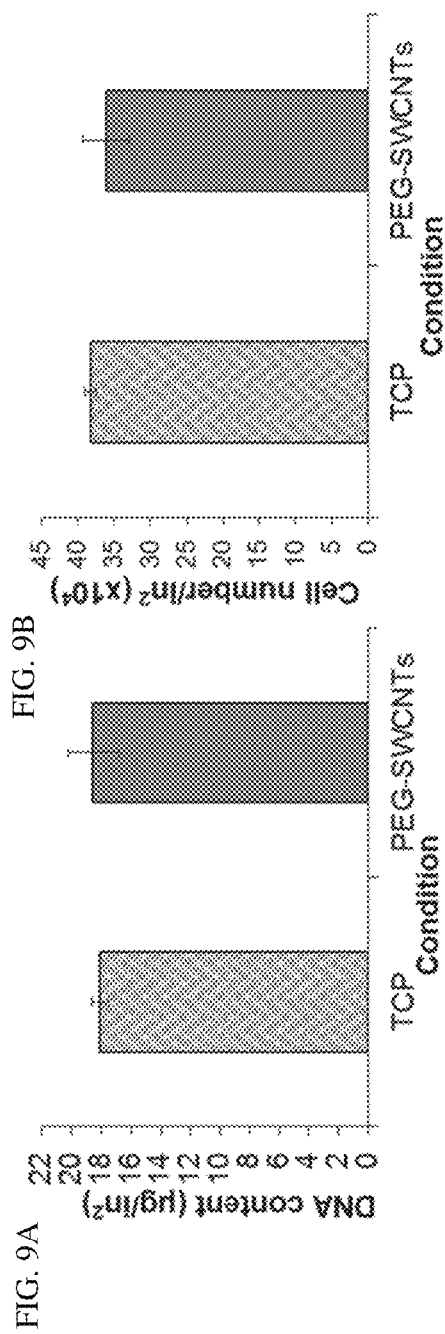
FIG. 9A is a graph depicting DNA content of cells seeded on TCP and PEG 1-SWCNTs nanocomposite.
FIG. 9B is a graph depicting total number of cells seeded on TCP and PEG 1-SWCNTs nanocomposite.

PC12 cell viability on a representative PEG 2-SWCNTs nanocomposite (FIG. 9) by measuring the DNA content via a standard PicoGreen assay (FIG. 9A) and cell metabolic activity via a standard Reazurin assay (FIG. 9B). Double-stranded DNA content was measured by a PicoGreen assay and normalized by substrate surface area. (FIG. 9A) Cell number was measured by a Resazurin assay and normalized by substrate surface area. PC12 cells were seeded at 40 000 per well and cultured for 24 hours prior to viability measurements. Both methods indicated that there was no significant difference in cell viability between the TCP control and the PEG 2-SWCNTs nanocomposites.

The results presented herein demonstrate a new method for transferring aligned SWCNTs onto hydrogel. The transfer method advantageously allows for >99% SWCNT transfer efficiency. The method is compatible with various hydrogels. The method does not require immediate steps or sacrificial substrates making the method simpler than prior art strategies. The hydrogel-SWCNT composite substrates can be used in various tissue engineering and sensing applications.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for transferring a carbon nanotube, the method comprising:
   providing a substrate;
   preparing a carbon nanotube on the substrate to prepare a carbon nanotube-coated substrate;
   applying a hydrogel precursor solution to the carbon nanotube-coated substrate;
   applying a polymeric film to the hydrogel precursor solution;
   polymerizing the hydrogel precursor solution to form a hydrogel; and
   removing the hydrogel from the substrate, wherein the hydrogel comprises the carbon nanotube, using the polymeric film to transfer the carbon nanotube.

2. The method of claim 1 further comprising aligning the carbon nanotubes on the substrate.

3. The method of claim 1 wherein the substrate comprises a quartz wafer.

4. The method of claim 1 wherein the carbon nanotube-coated substrate is prepared with a solvent selected from the group consisting of water and alcohol.

5. The method of claim 4 wherein the alcohol is selected from the group consisting of isopropyl, ethanol, and methanol.

6. The method of claim 1 wherein the carbon nanotube has a density ranging from about 25% to about 55%.

7. The method of claim 1 wherein the carbon nanotube has a length ranging from about 2 µm to about 5 µm.

8. The method of claim 1 wherein the hydrogel precursor solution is selected from a natural hydrogel, a synthetic hydrogel, and combinations thereof.

9. The method of claim 8 wherein the natural hydrogel precursor solution is selected from the group consisting of alginate, chitosan, silk, agarose, collagen, gelatin, fibrinogen, fibrin, laminin, fibronectin, carboxymethyl cellulose, hyaluronan, and combinations thereof.

10. The method of claim 8 wherein the synthetic hydrogel precursor solution is selected from the group consisting of polyvinyl alcohol (PVA), pHEMA, poly-lactic-co-glycolic acid, polylactic acid, polyglycolic acid, polyacrylamide, poly(ethylene glycol), polypropylene glycol, polyurethane, polyvinylpyrrolidone, methyl cellulose, poly(ethylene glycol) diacrylate (PEGDA), PEG-vinyl sulfone, PEG-amine, PEG-dimethacrylate, PEG-dithiol, PEG-polylactic acid co-polymers (PEG-PLA), PEG-maleimide, PEG-biotin, PEG-butyraldehyde, PEG-carboxymethyl, co-polymers thereof, and combinations thereof.

11. The method of claim 1 wherein the carbon nanotube is a single-wall carbon nanotube.

12. The method of claim 11 wherein the single-wall carbon nanotube has a diameter ranging from about 1 nm to about 3 nm.

* * * * *